United States Patent [19]
Greenwood

[11] Patent Number: 6,082,181
[45] Date of Patent: Jul. 4, 2000

[54] ULTRASONIC FLUID DENSITOMETER HAVING LIQUID/WEDGE AND GAS/WEDGE INTERFACES

[75] Inventor: Margaret S. Greenwood, Richland, Wash.

[73] Assignee: Battelle Memorial Institute, Richland, Wash.

[21] Appl. No.: 09/178,031

[22] Filed: Oct. 21, 1998

[51] Int. Cl.[7] .............................. G01N 9/24; G01N 29/02
[52] U.S. Cl. ............................ 73/32 A; 73/1.03; 73/1.83
[58] Field of Search .................... 73/32 A, 1.02, 73/1.83, 1.86, 54.41, 1.03

[56] References Cited

U.S. PATENT DOCUMENTS

| | | | |
|---|---|---|---|
| 4,149,139 | 4/1979 | Kronk | 367/93 |
| 4,320,659 | 3/1982 | Lynnworth et al. | 73/589 |
| 4,571,693 | 2/1986 | Birchak et al. | 73/589 |
| 4,821,838 | 4/1989 | Chen | 181/175 |
| 4,893,496 | 1/1990 | Bau et al. | 73/32 A |
| 4,991,124 | 2/1991 | Kline | 73/32 A |
| 5,365,778 | 11/1994 | Sheen et al. | 73/54.41 |
| 5,708,191 | 1/1998 | Greenwood et al. | 73/32 A |
| 5,886,250 | 3/1999 | Greenwood et al. | 73/32 A |

OTHER PUBLICATIONS

"Noninvasive Sensor Measures Fluid Density and Viscosity," *Sensors* Oct., 1994, pp. 13 and 15.

Sheen et al., "An In–Line Ultrasonic Viscometer," *Review of Progress in Quantitative Nondestructive Evaluation*, vol. 14a pp. 1151–1158, 1995.

*Primary Examiner*—John E. Chapman
*Attorney, Agent, or Firm*—Paul W. Zimmerman

[57] ABSTRACT

The present invention is an ultrasonic liquid densitometer that uses a material wedge having two sections, one with a liquid/wedge interface and another with a gas/wedge interface. It is preferred that the wedge have an acoustic impedance that is near the acoustic impedance of the liquid, specifically less than a factor of 11 greater than the acoustic impedance of the liquid. Ultrasonic signals are internally reflected within the material wedge. Density of a liquid is determined by immersing the wedge into the liquid and measuring reflections of ultrasound at the liquid/wedge interface and at the gas/wedge interface.

12 Claims, 4 Drawing Sheets

ULTRASONIC FLUID DENSITOMETER HAVING LIQUID/WEDGE AND GAS/WEDGE INTERFACES

This invention was made with Government support under Contract DE-AC06-76RLO 1830 awarded by the U.S. Department of Energy. The Government has certain rights in the invention.

FILED OF THE INVENTION

The present invention is an apparatus and method for measuring fluid density. More specifically, the invention relies upon internal reflection of ultrasonic signals from both a liquid/wedge interface and a gas/wedge interface to provide either on-line calibration, a third signal improved accuracy densitometry or a combination thereof.

BACKGROUND OF THE INVENTION

Use of sound waves, specifically ultrasonic sound waves for determining fluid density is well known. An ultrasonic sensor for measuring fluid density was reported by S. Sheen at Argonne National Laboratory. It received a R&D 100 Award in 1994 and a description appeared in the Research and Development magazine in October, 1994, p.15.

Sheen describes an ultrasonic densitometer (FIG. 1) for measuring a density of a fluid 100. The ultrasonic densitometer has a wedge material 102 wherein the wedge material 102 has at least two sides substantially parallel. A first parallel side 104 has a first ultrasonic transducer 106 mounted thereon and a second parallel side 108 immersible into said fluid (liquid/wedge interface) whereby a first portion of an ultrasonic signal emanating from said first ultrasonic transducer 106 strikes the second parallel side 108 and reflects back to the first parallel side 104 providing a reflection coefficient. A second portion of the ultrasonic signal propagates through the fluid 100, strikes a second wedge immersed surface 110 and reflects back to the first ultrasonic transducer 106 providing a speed of sound in the fluid. The arm surfaces 112 of the T are in contact with air (gas/wedge interface) for reference measurements. The T-shaped wedges 102 are mounted through the wall of a pipe 114 so that the fluid 100 within the pipe passes between the immersed surfaces 108, 110 of the two T-shaped wedges 102, 102a. From the reflection coefficient and the speed of sound in the fluid, the density of the fluid is obtained. In a second paper S. H. Sheen, H. T. Chien, and A. C. Raptis, "An In-Line Ultrasonic Viscometer," Review of Progress in Quantitative Nondestructive Evaluation, Vol. 14a, pp 1151–1158, 1995, Sheen specifies that the T-shaped wedge material is aluminum. The second transducer generates shear waves used for determining viscosity. A disadvantage of Sheen's ultrasonic densitometer is that because the wedge material is aluminum, the acoustic impedance of the wedge material is much greater than the acoustic impedance of the fluid so that a substantial change in density (eg. 10%) results in a quite small change in the aluminum/liquid reflection coefficient of about 0.014. Secondarily, the ultrasonic signal is required to reflect through the fluid of interest thereby requiring the requisite target surface of a second T-shaped wedge. Further, for fluids attenuative of ultrasound, density measurements would not be obtainable.

Another ultrasonic fluid meter is described in M. S. Greenwood, J. L. Mai, and M. S. Good, "Attenuation measurement of ultrasound in a kaolin-water slurry: A linear dependence upon frequency," A J. Acoust. Soc. Am. 94, 908–916 (1993

This ultrasonic attenuation sensor was developed for concentration measurements in a $^1\!/_{12}$-scale model of a double-shell tank. Because fluid density is a function of concentration, this unit may be used to determine fluid density as well as fluid concentration. The sensor consists of a send transducer and a receive transducer, separated by 4 inches. The ultrasound produced by the send transducer travels through a liquid (or slurry) where it is attenuated. The signal recorded by the receive transducer indicates how much attenuation has occurred. However, the instrument required calibration by making measurements in the laboratory for that specific slurry formulation so that concentration of the slurry could be correlated with voltage of signal in receive transducer. Again, this ultrasonic densitometer required that the ultrasonic signal be detected after passing through the fluid, in this case slurry, of interest and further required prior laboratory calibration.

Commercially available ultrasonic fluid concentration measuring devices are available through JM Science Inc, Buffalo, N.Y., Manufactured by: Fuji Ultrasonic Engineering Co., Ltd. In operation, an ultrasonic transducer produces ultrasound that propagates through the fluid of interest then is reflected by a metal plate about an inch away from the transducer. The reflected signal returns to the transducer and the time for a round trip is determined. Since the distance is known, the velocity of ultrasound in the liquid can be determined. The Fuji sensor correlates the speed of sound with a concentration of a particular fluid solution and with temperature of the particular fluid solution and requires laboratory calibration. As with Greenwood et al., the reflected ultrasonic signal must pass through the fluid of interest and the instrument requires calibration.

There is a need in the field of ultrasonic densitometry for an ultrasonic fluid densitometer that has greater sensitivity, and does not require a reflected signal to pass through the fluid of interest.

SUMMARY OF THE INVENTION

The present invention is an ultrasonic fluid densitometer that uses a material wedge having an acoustic impedance that is near the acoustic impedance of the fluid, specifically less than a factor of 11 greater than the acoustic impedance of the fluid. The invention also includes a wedge having at least two transducers for transmitting and receiving ultrasonic signals internally reflected within the material wedge. Density of a fluid is determined by immersing the wedge into the fluid and measuring reflection of ultrasound at the wedge-fluid interface.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
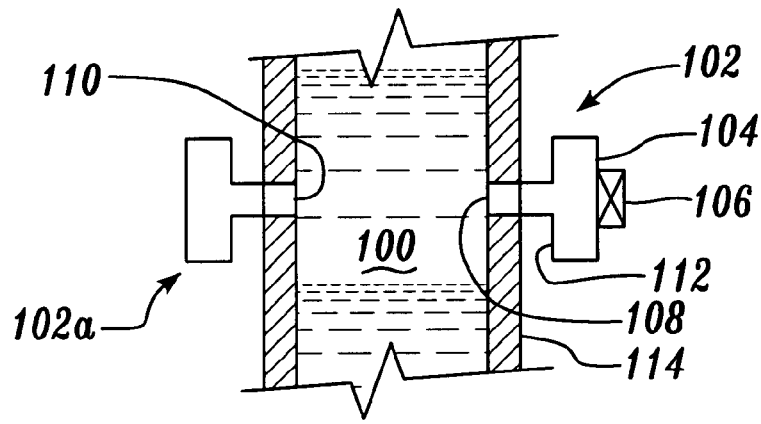
FIG. 1 is a cross section of a prior art ultrasonic densitometer.

According to the present invention it is preferred that the fluid 100 and the wedge material 102 have a ratio of an acoustic impedance of the wedge material to an acoustic impedance of the fluid that is less than 11. Table 1 shows acoustic impedances for candidate wedge materials and ratio of acoustic impedance of those materials to the acoustic impedance of water which has an acoustic impedance of 1.5 ($10^6$) kg/m$^2$s. By using a wedge material 102 having an acoustic impedance ratio to the fluid of less than 11, there is an increased change in reflection coefficient which increases the sensitivity of the ultrasonic densitometer. Specifically for Rexolite (C-LEC Plastics, Inc. Beverly, N.J.), for a 10% change in fluid density, there is a change of about 0.05 of the reflection coefficient.

TABLE 1

| Acoustic Impedances | | |
|---|---|---|
| Material | Acoustic Impedance(kg/m$^2$s) | Ratio to Water |
| Aluminum | 17($10^6$) | 11.33 |
| Lead | 25($10^6$) | 16.67 |
| Steel | 45($10^6$) | 30.00 |
| Rexolite | 2.5($10^6$) | 1.67 |

It is preferred that the acoustic impedance ratio be less than about 5 and more preferably less than about 3 when the fluid is a liquid. Plastic includes polymers including but not limited to Rexolite, Loten (Sigma Transducers, Kennewick, Wash.), and acrylics. It is further preferred that the reflection coefficient transition from positive to negative with a zero value in between. Rexolite demonstrates this behavior with positive reflection coefficient above 38° angle of internal reflection and negative reflection coefficient below 38°. In contrast, some other wedge materials (including other plastics and metals) have a negative value of the reflection coefficient for all angles when the base is immersed in liquids. A transducer pair may be mounted forming an angle with the fluid interface at any angle with respect to the perpendicular to the wedge base. However, the determination of the density is more accurate for a larger difference in angle between the two transducer pairs. For example, the two transducer pairs might have angles of 5 degrees and 60 degrees. Accordingly, in a preferred embodiment, at least one pair of transducer is mounted with five to ten degrees of the perpendicular to the wedge base.

In a preferred embodiment, at least two temperature sensors are used, one on the liquid contact surface and one on an upper surface of the wedge material to confirm temperature uniformity of the wedge material.

Fluids that can be measured are preferably liquid. A liquid may be a liquid solution, or mixture having solid particles or immiscible phases. Immiscible phases include liquids and gases. In mixtures, it is preferred that the non-soluble phase be of a size smaller than a wavelength of the ultrasonic waves. It is further preferable that the mixture be homogenous and may require mixing. When a gas (eg air) phase is present, it is preferred to use a minimum measurement in a series of measurements to obtain the most accurate measure of density. The reason is that gas bubbles may adhere to the surface of the immersed wedge material and increase the reflectance of ultrasound at the wedge material-gas interface.

Figure 2:
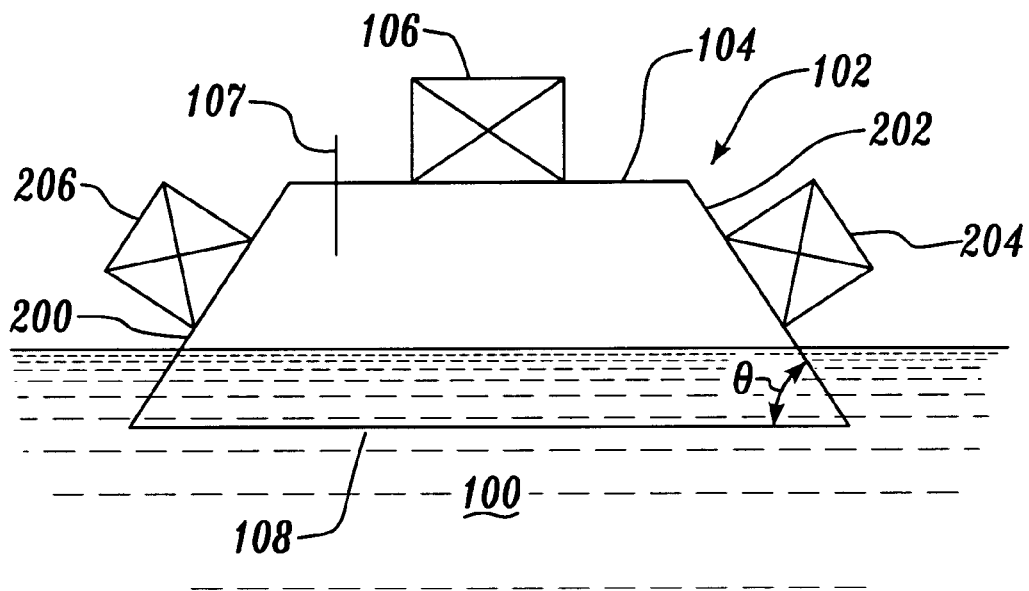
FIG. 2 is a three transducer embodiment of the present invention.
Figure 3:
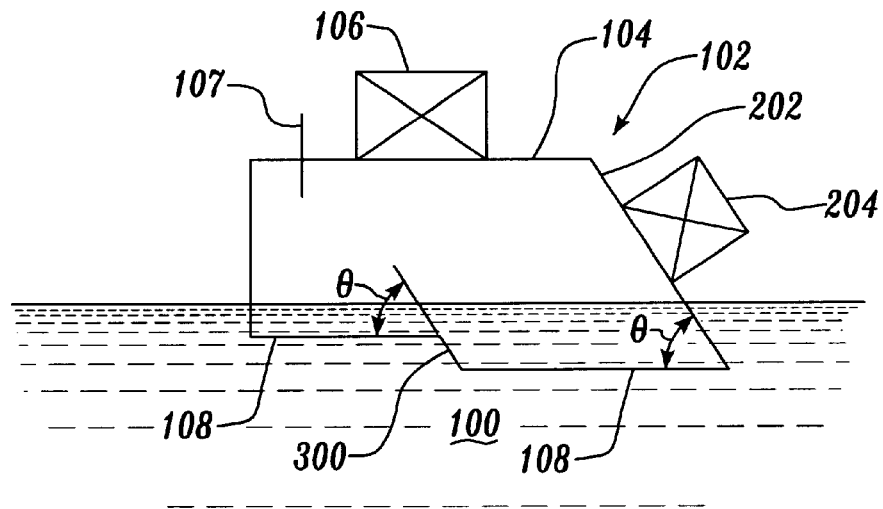
FIG. 3 is a two transducer embodiment of the present invention.
Figure 4:
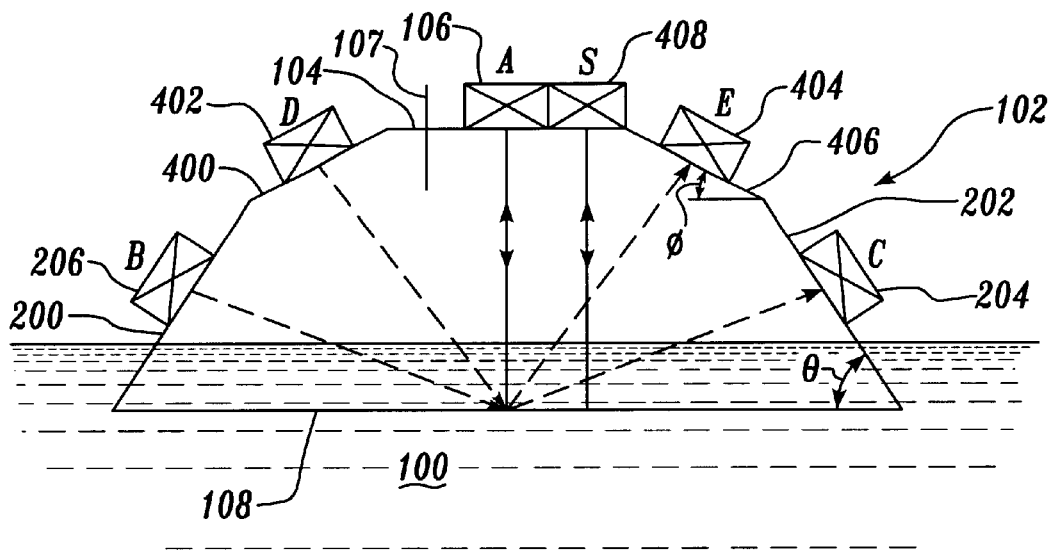
FIG. 4 is a six transducer embodiment of the present invention.

A further advantage is realized when all detected ultrasonic signals are detected on the basis of ultrasonic reflections internal to the wedge material. The embodiments shown in FIGS. 2, 3, 4, 5a have a wedge material 102 having at least two sides substantially non-parallel. In FIGS. 2, 3, 4, a first parallel side 104 has a first ultrasonic transducer 106 mounted thereon and a second parallel side 108 immersible into said fluid whereby a first portion of an ultrasonic signal emanating from said first ultrasonic transducer 106 strikes the second parallel side 108 and reflects back to the first parallel side 104. The wedge material 102 further has (a) a second ultrasonic transducer a first non-parallel side 200, from which emanates a second reflected ultrasonic signal toward a second non-parallel side 202; and (b) a receiving ultrasonic transducer 204 mounted on the second non-parallel side 202 for receiving the second reflected ultrasonic signal.

In FIG. 2, each of the first and second non-parallel sides 200, 202 is connected to the first and second parallel sides 104, 108. A transmitting transducer 206 is mounted on the first non-parallel side 200 whereby the transmitting transducer transmits said second ultrasonic signal that reflects from said second parallel side 108 creating the second reflected ultrasonic signal that is received by the receiving transducer 204.

In FIG. 3, the first non-parallel side 300 is a cut in the second parallel side 108 and the second non-parallel side 202 is connected to the first and second parallel sides 104, 108, whereby an ultrasonic signal transmitted by the first transducer is reflected by both the second parallel side 108 and the first non-parallel side 300 producing a reflected signal from the second parallel side 108 to the first transducer and producing said second reflected signal from the first non-parallel side 300 to the receiving transducer 204. For the embodiments shown in FIGS. 2 and 3, it is necessary to know a-priori the speed of sound in the wedge material 100 and the sign (positive or negative) of the reflection coefficient for the wedge material/fluid combination.

The angle theta of the non-parallel sides 200, 202, 300 to the second parallel side 108 is critical to the present invention for sensitivity to small changes in fluid density. An angle of 20 degrees provided limited sensitivity whereas an angle of about 60 degrees provided greater sensitivity to changes in fluid density. Accordingly, the angle theta is preferable greater than about 20 degrees, more preferably greater than about 30 degrees, and most preferably about 40 degrees.

The FIG. 4 embodiment is similar to the one shown in FIG. 2 but having additional sides and transducers permitting in-situ measurement of speed of sound in the wedge material and in-situ determination of the sign of the reflection coefficient. More specifically, a third non-parallel side 400 has a second transmitting ultrasonic transducer 402 that emits a third ultrasonic signal that reflects from the second parallel side 108 and creates a third reflected ultrasonic signal that is received by a second receiving ultrasonic transducer 404 mounted on a fourth non-parallel side 406. The third and fourth non-parallel sides 400, 406 make a second angle phi with said first parallel side different from the first angle theta. These additional sides and transducers are used to determine the sign of the reflection coefficients. Alternatively, analysis of signal phase may be done to determine the sign of the reflection coefficient without using the second transmitting and receiving transducers 402, 404. However, additional electronic circuitry and possibly additional software for data reduction would be needed for analysis of signal phase, which is less preferred. A fourth transmitting ultrasonic transducer 408 is mounted on the first parallel side 104 for determination of the speed of sound of the shear wave in the wedge material 102. The speed of sound of the longitudinal wave is measured by the pulse-echo measurement or by a pitch-catch measurement.

The transducers may be any ultrasonic transducers, preferably emitting in a range from about 0.5 MHZ to about 10 MHZ.

Electrical signals from the transducers may be collected for analysis in at least two ways. In one way, A function generator (not shown) may be applied to the transmitting transducer 206. The ultrasound reflected at the second parallel side 108 of the wedge material 102 produces a response in the receive transducer 204. This RF-signal, after amplification (r attenuation) by a receiver (not shown) may be sent to a peak detector (not shown). After selecting a window around the RF-signal of interest, the peak detector outputs a DC-voltage that is proportional to the maximum of the RF-voltage in the window.

Alternatively, a 12-bit digitizer may be used so that extremely small changes in the voltage can be detected. When a 12-bit digitizer is used, the maximum value of the signal will be determined using software. A multiplexer system will sequentially send the toneburst signal to each send transducer and obtain the return signal. An algorithm will be developed to take averages and, in the case of the slurry, to look for minimum values in the signal and to process this data to produce an on-line value of the density and velocity of sound.

Figure 6:
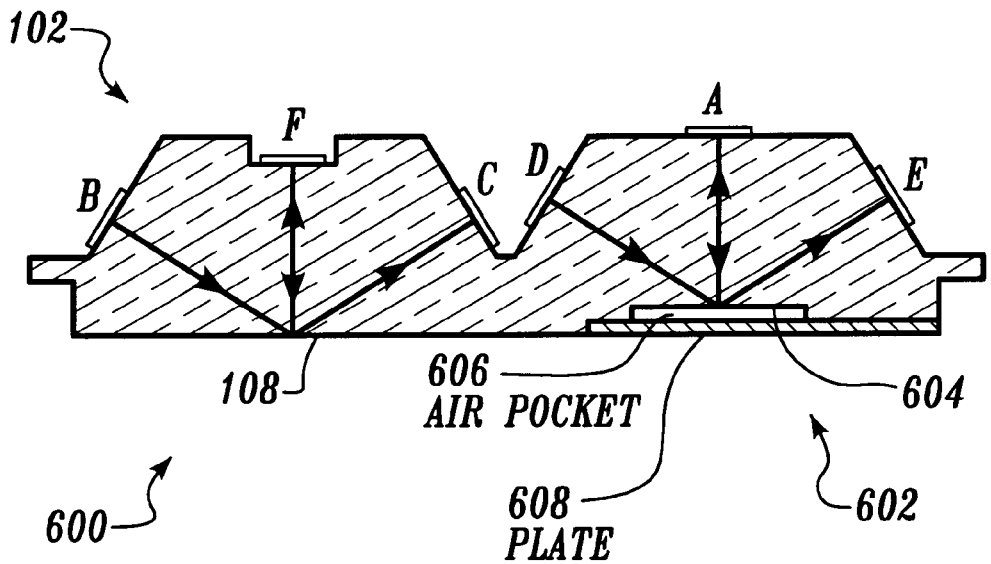
FIG. 6 is a densitometer with a liquid/wedge interface and a gas/wedge interface with pitch catch and pulse echo transducers.

The preferred embodiment having both a liquid/wedge interface and a gas/wedge interface is shown in FIG. 6. This embodiment can provide on-line calibration, three signal density measurements or both. There are nearly-identical sections, where the path lengths in wedge material 102 are the same for corresponding transducers. In the liquid/wedge interface section 600 the ultrasound interrogates the liquid (not shown) (which may be a slurry) properties by striking the base 108 immersed in the liquid. In the gas/wedge interface section 602 the ultrasound strikes the base 604 immersed in the gas (preferably air) to provide the reference voltages.

The gas/wedge interface 602 may simply be open to a gas or to the atmosphere. It is preferred as shown in FIG. 6 that a portion be removed from the wedge material 102 to form a gas pocket 606 and a plate 608 sealed to the bottom of the wedge material gas/wedge interface section 602 to maintain the air pocket and prevent egress of liquid into the gas pocket 606. Ultrasound strikes the top surface 604 of the air pocket 606 where it is reflected; ultrasound is not transmitted into the air pocket 606. By having both sections 600, 602 in contact with the liquid, the temperature distributions in the left and right sections are expected to be very close, if not identical. In addition, heating (preferably electrical heating) of the wedge material 102 can be used to maintain a uniform temperature throughout the wedge material 102. In the new design the Rexolite-liquid interface is in the near field or slightly beyond the near field, and the receive transducer is also in the near field or just slightly beyond the near field region. In the near field region the rays do not diverge and the reflection coefficient for a single ray applies exactly.

The voltages measured on the liquid/wedge interface side 600 provide information about the liquid or slurry and those on the gas/wedge interface side 602 provide the reference voltages. The reflection coefficient is measured from a phase change between the signal reflected from the gas/wedge interface 602 and that reflected from the liquid/wedge interface 600. Software can be used to determine whether there is a 180° phase shift or not. When ultrasound reflects from air, the reflection coefficient for all angles is negative. If the phase is the same as for air, the reflection coefficient has a negative value; if not, a positive value.

If six transducers (A–F) are used as shown in FIG. 6, then the existing printed circuit board can be used because it contains two pulse-echo channels and two pitch-catch channels. If, however, a third angle, as in FIG. 4 (40–42°), is desired, then an additional board and multiplexing would be needed.

The previous analysis of embodiment in FIG. 4 used angles of 0° and 60° for determining the value of the density, while the third angle (40–42°) was used to determine the sign of the reflection coefficient.

With the dual interface embodiment of FIG. 6, the sign of the reflection coefficient may be determined by examining the phase shift between the signals from the liquid and gas. In that case, the third angle can be used to determine the density, which increases the accuracy of the density measurement. In order to use the third angle in the determination of the density, a chi-squared analysis may be used.

$$X^2 = \sum_{i=1}^{3} [RCX_i - RCT_i(\text{constants}, Z, c)]^2 / \sigma_i^2 \quad (1)$$

wherein Z is the acoustic impedance of the fluid, c is the speed of sound in the fluid, $\sigma_i$ is the error associated with the i th measurement;

RCX is the experimental value of the reflection coefficient at a given angle and RCT is the theoretical value $R_{LL}$ calculated using $$R_{LL} = (1/N)(G-H+J) \quad (2)$$

where $G = (c_T/c_L)^2 \sin 2\theta_L \sin 2\theta_T$ $H = \cos^2 2\theta_T$ $J = Z \cos \theta_L / \rho_s c_L \cos \theta$ $N = G + H + J$ $Z = \rho c \quad (3)$ $\theta_L$ is the angle of incidence that the longitudinal ultrasonic ray makes with a normal to the surface. When a longitudinal ultrasonic ray strikes the surface at an angle, a reflected longitudinal wave and a mode-converted shear wave result. $\theta_T$ is the angle that the shear wave makes with a normal to the surface. $\theta$ is the angle at which the ultrasonic ray is transmitted into the liquid. $C_L$ is the longitudinal speed of sound in the wedge material. $C_T$ is the shear speed in the wedge material. $\rho_s$ is the density of the solid or wedge material, and $\rho$ is the density of the liquid.

The term "constants" in Eq. 1 indicates known values of the wedge material and known angles. The objective is to find the value of the acoustic impedance and speed of sound c so that chi-squared has a minimum value. Density is then obtained from acoustic impedance and speed of sound. A numerical method is used to determine this minimum value. The steps in this analysis are as follows:

(1) The analysis using 0° and 60° angles is used to determine the "approximate" values of the acoustic impedance and speed of sound. The third angle (40–42°) is used for the chi-squared analysis.

(2) Then a two-dimensional matrix of values around these two approximate values is set up and the value of chi-squared is calculated.

(3) The two-dimensional matrix is searched for the minimum value of chi-squared and this corresponds to the best values for the acoustic impedance and speed of sound.

(4) Convert the acoustic impedance and the speed of sound to a density with Eq. (3).

Figure 7:
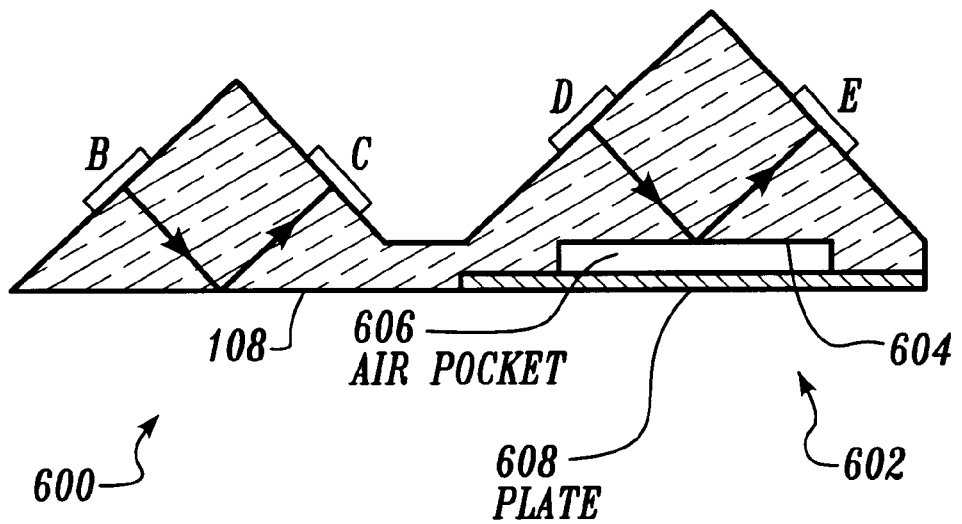
FIG. 7 is a densitometer with a liquid/wedge interface and a gas/wedge interface with pitch catch transducers.

In FIG. 7, transducers A and F are omitted. Transducers B and C are preferably mounted at an angle of about 40°. Transducer B is the send transducer and transducer C is the receive transducer. The voltage from C and the temperature of the wedge are monitored or measured. Transducers D and E are used to provide a calibrating voltage at receiving transducer E for a given temperature of the wedge and with a reflection from a wedge/gas interface.

EXAMPLE 1

Figure 5A:
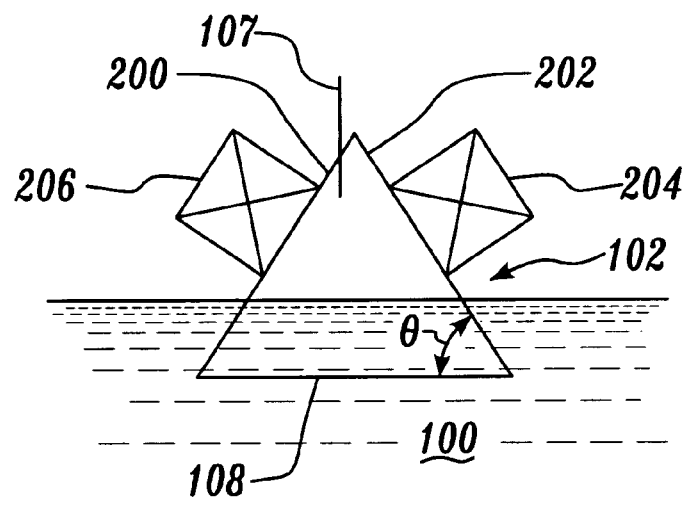
FIG. 5a is a pitch-catch block for experiments.
Figure 5B:
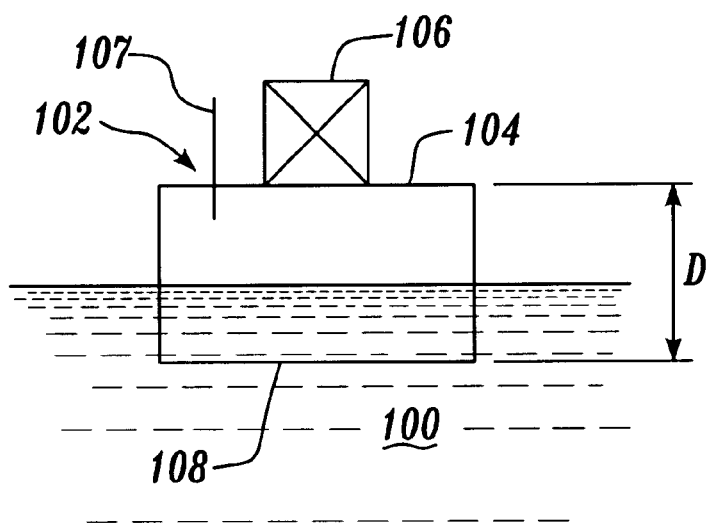
FIG. 5b is a pulse-echo block for experiments.

An experiment was conducted to demonstrate the ultrasonic densitometer of the present invention. For the experiment, two wedges were used. FIG. 5a and FIG. 5b shows the experimental setup for the pitch-catch mode, FIG. 5a, and the pulse-echo mode, FIG. 5b. The wedge material 102 is Rexolite. For the pitch-catch, FIG. 5a, the wedge material is an equilateral triangular solid with an angle theta of about 60 degrees. For the pulse-echo, FIG. 5b, the distance D between the first transducer 106 and the second parallel side 108 was 2.7 cm.

A 12-cycle toneburst at a frequency of 2.25 MHZ, produced by the Wavetek 901 function generator, was applied to the transmitting transducer 206. The ultrasound reflected at the second parallel side 108 of the wedge material 102 produced a response in the receive transducer 204. This RF-signal, after amplification (or attenuation) by an MR101 receiver, was sent to a Panametrics GPD-5052 peak detector. After passing through an RC circuit with a time constant of 10 milliseconds to minimize fluctuations, the DC voltage was measured by a DC-voltmeter to any accuracy of three decimal places.

The reflection coefficient was determined by comparing the amplitude of the RF-voltage (or toneburst) of the received signal (or echo) when the second parallel side 108 of the wedge material 102 is immersed in the liquid with that when it is air. Since the voltage of the received signal is directly proportional to the pressure and to the reflection coefficient, the following relationship is obtained:

$$Rc_{liq} = Rc_{air}(V_{liq}/V_{air})$$

where

RC is reflection coefficient, and

V is voltage from the transducer.

The reflection coefficient is a function of (1) density of the wedge material 102, (2) speed of sound of the longitudinal wave, (3) speed of sound of the shear wave, (4) the angle of incidence of the longitudinal wave with respect to the second parallel side 108, (5) the density of the fluid, and (6) the speed of sound in the fluid (See J. Krauthkramer and H. Krauthkramer, *Ultrasonic Testing of Materials*, Springer-Verlag, Third Edition, 1983, pp 606–607, Equation A.10). By obtaining measurements at two angles, pulse echo at zero degrees and pitch-catch at another angle, two equations for the reflection coefficients are provided having the unknowns of density of the fluid and speed of sound in the fluid.

The speed of sound in Table E1-1 was measured using the time-of-flight method having an uncertainty of about 2%.

The fluid used in this experiment was water with varying amounts of sugar. Samples 2–8 received increasing amounts of sugar. The sugar was commercially available cane sugar. Table E1-1 shows the density obtained by weighing fluid samples in a 50-ml volumetric flask. Table E1-1 also shows the voltage ratio data for reflection coefficients obtained using the pulse-echo block pitch-catch block with a 60 degree angle. In each case an average DC-voltmeter reading was obtained when the interface was immersed in the liquid and when in air. From this voltage ratio data, the reflection coefficients were derived.

TABLE E1-1

Parameter Standards For Water Samples

| Sample | Sugar Conc. | Density kg/m³ | Speed of Sound (m/s) | Pitch-Catch $V_{liq}/V_{air}$ | Pulse-echo $V_{liq}/V_{air}$ |
|---|---|---|---|---|---|
| 1 | 0.00 | 997 | 1483 | 0.3245 | 0.2477 |
| 2 | >0.00 | 1011 | 1498 | 0.3454 | 0.2380 |
| 3 | >0.00 | 1024 | 1510 | 0.3625 | 0.2287 |
| 4 | >0.00 | 1036 | 1523 | 0.3802 | 0.2193 |
| 5 | >0.00 | 1055 | 1537 | 0.4052 | 0.2066 |
| 6 | >0.00 | 1060 | 1542 | 0.4133 | 0.2016 |
| 7 | >0.00 | 1070 | 1554 | 0.4265 | 0.1942 |
| 8 | >0.00 | 1087 | 1567 | 0.4514 | 0.1805 |

The objective is to convert the pulse-echo at zero degrees and pitch-catch at degrees RF-voltage ratios to reflection coefficients, solve the inverse problem to obtain the density and velocity of sound in the liquid, and compare them with the densities and velocities of sound shown in Table E1-1.

The reflection coefficient is very sensitive to the longitudinal wave velocity and the shear wave velocity. This sensitivity has been used to determine these velocities to four significant figures. These values will be used in all further calculations: longitudinal wave velocity in Rexolite $c_L=2337$ m/s, shear wave velocity in Rexolite $c_T=1157$ m/s. A reflection coefficient is obtained by multiplying the RF-voltage ratio by the reflection coefficient for air. The reflection coefficient for air at OE is −1.00 and at 60E, +0.4170. Table E1-2 give the ultrasonically derived velocities of sound and densities of the eight liquid samples.

TABLE E1-2

Ultrasonically Derived Parameters

| Sample | Speed of Sound(m/s) | % error | Density (kg/m³) | % error |
|---|---|---|---|---|
| 1 | 1481 | −0.13% | 988.9 | 1.10% |
| 2 | 1498 | 0.00% | 1007.0 | −0.44% |
| 3 | 1503 | −0.46% | 1024.2 | −0.02% |
| 4 | 1510 | −0.85% | 1039.6 | 0.33% |
| 5 | 1522 | −0.98% | 1059.1 | 0.40% |
| 6 | 1519 | −1.50% | 1072.1 | 1.10% |
| 7 | 1522 | −2.10% | 1086.8 | 1.61% |
| 8 | 1527 | −2.60% | 1114.8 | 2.60% |

There is very good agreement between the two sets of measurements. These results show that using two reflection coefficients is a viable method for determining the density and the velocity of sound in an aqueous solution to an accuracy of at least 3%.

EXAMPLE 2

An experiment was conducted to use the present invention with non-aqueous liquids. The same apparatus as described in Example 1 were used. Results are shown in Table E2-1

TABLE E2-1

Non-aqueous liquids

| Sample | Liquid | Density (kg/m$^3$) | Density Error | Speed of Sound(m/s) | Sound Error |
|---|---|---|---|---|---|
| 9 | 2-propanol | 782.6 | −0.72% | 1157.3 | −1.4% |
| 10 | Paraffin Oil | 877.2 | 3.12% | 1470.6 | −6.6% |

Reasonable agreement was achieved with non-aqueous fluids.

EXAMPLE 3

An experiment was conducted to demonstrate measuring the average bulk density of an aqueous slurry with the present invention. The apparatus described in Example 1 was used.

A slurry was mixed using Potter's silicon dioxide particulate (Type 13) in water. The particulate had a maximum diameter of 0.00381 cm. For ultrasound produced by a 2.25 MHZ transducer, the wavelength in water is 0.066 cm. Since the resolution of a wave is approximately equal to its wavelength, the ultrasound should not be able to resolve individual particles in this slurry and measurements should, therefore, determine the average density and average velocity of sound.

The slurry was placed in a 2000 ml beaker and a mixer kept the slurry from settling. The slurry had a density of 1143.1 kg/m$^3$.

Calculations of ultrasonic data were carried out for the slurry and yielded a density of 988 kg/m$^3$, which is 13.6% low compared to the actual density. The source of the problem seemed to be that the mixer was aerating the slurry. The wedge material was re-oriented to a vertical position to minimize accumulation of air bubbles. In addition, the method of taking the measurements was altered. Instead of taking the average value of the voltmeter readings, the minimum value that repeated within a 30–60 second interval (to the second decimal place) was recorded. This reading would correspond to a minimum effect due to air and would give a truer reading of the slurry's non-aerated density.

Additional slurry samples were then subjected to the modified experimental procedure with results shown in Table E3-2.

TABLE E3-2

Slurry Sample Density Data

| Sample | Density (kg/m$^3$) | Ultrasonic Density (kg/m$^3$) | Percent Error |
|---|---|---|---|
| S-1 | 1143.1 | 1083.2 | −5.24% |
| S-2 | 1097.3 | 1069.9 | −2.49% |
| S-3 | 1077.0 | 1049.8 | −2.52% |
| S-4 | 1050.4 | 1051.6 | 0.11% |

TABLE E3-2-continued

Slurry Sample Density Data

| Sample | Density (kg/m$^3$) | Ultrasonic Density (kg/m$^3$) | Percent Error |
|---|---|---|---|
| S-5 | 1037.6 | 1041.3 | 0.36% |
| S-6 | 1065.5 | 1.53.6 | −1.11% |

There is only one sample with an error at about 5%. All other samples are within 3%.

EXAMPLE 4

Using the Rexolite wedge materials as in Example 1, (FIG. 5a and FIG. 5b) and glycerine as the fluid, it was discovered that the pulse-echo signal was so weak as to be essentially non-existent. This was because the acoustic impedance of glycerine nearly matches the acoustic impedance of Rexolite ($2.5(10^6)$kg/m$^2$s). Accordingly, a different plastic material would be used for the pulse-echo wedge material.

EXAMPLE 5

Analysis of a model problem was considered for a sugar water solution having a known density of 1083.0 kg/m$^3$ and a known speed of sound of 1564.3 m/s. The reflection coefficients were calculated for three angles and then varied slightly to yield the "experimental" reflection coefficients. Values of the standard deviation a were also assigned. Ten values of the density between 1080.5 kg/m$^3$ and 1085.0 kg/m$^3$ and ten values of the speed of sound between 1559.30 m/s and 1568.30 m/s were used to calculate a 10×10 matrix of chi-squared. However, this matrix yielded several local minima! When the values of the acoustic impedance were calculated for each minimum, the values were the same. This indicated that the acoustic impedance and the speed of sound were the primary variables. Thus a matrix obtained by varying the acoustic impedance and the speed of sound was used instead. That is, the analytical equations were rewritten in terms of acoustic impedance of the liquid rather than density. After determining the values of the acoustic impedance and speed of sound that yield the minimum value of chi-squared, the density was obtained.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An ultrasonic densiometer for measuring a density of a liquid, said ultrasonic densiometer having a wedge material, said wedge material having at least two sides substantially parallel, a first parallel side having a first ultrasonic transducer mounted thereon and a second parallel side immersible into said liquid as a liquid/wedge interface whereby a first ultrasonic signal emanating from said first ultrasonic transducer strikes said second parallel side and reflects back to said first parallel side as a first angle, said wedge material further having a third side substantially parallel to the first side, said third side in contact with a gas forming a gas/wedge interface whereby a second ultrasonic signal emanating from the first ultrasonic transducer and reflected from the non-parallel side strikes said third parallel side; the improvement comprising:

said liquid/wedge interface is on a first section of said wedge further having a pair of transducers mounted on a first pair of non-parallel sides as a second angle for a third ultrasonic signal emanating from one of said pair of transducers; and said gas/wedge interface is on a second section of said wedge, said second portion substantially ultrasonically similar to said first portion and having a second pair of non-parallel sides with transducers mounted thereon corresponding to said second angle.

2. The ultrasonic densitometer as recited in claim 1, wherein said gas/wedge interface is a gas pocket in said wedge material covered by a plate.

3. The ultrasonic densitometer as recited in claim 1, further comprising a third pair of non-parallel sides with transducers thereon as a third angle for obtaining ultrasonic reflection from the liquid/wedge interface.

4. A method of measuring density of a liquid comprising the steps of:

(a) placing a wedge material in contact with said liquid, said wedge material having a first section and a second section, said first section having a liquid/wedge interface, a first transducer mounted on a surface parallel to said liquid/wedge interface as a first angle, a second and third transducer as a first pair of transducers mounted on a first pair of opposing surfaces that are non-parallel to said liquid/wedge interface as a second angle, said second section having a gas/wedge interface and substantially ultrasonically similar to said first section and having two angles corresponding to the first and second angles of the first section;

(b) emitting ultrasonic signals from transmitting transducers to said liquid/wedge interface and to said gas/wedge interface;

(c) receiving reflected ultrasonic signals reflected from said interfaces;

(d) obtaining a set of parameters from said received reflected ultrasonic signals within said first section and from said received reflected ultrasonic signals within said second section; and (e) computing density from said sets of parameters.

5. The method as recited in claim 4, wherein said set of parameters is speed of sound and acoustic impedance obtained from said first section and a sign of a reflection coefficient obtained from said second section.

6. An ultrasonic densitometer for measuring a density of a liquid, said ultrasonic densitometer having a wedge material, said wedge material having a first section with at least two non-parallel sides, a first side having a first ultrasonic transducer mounted thereon and a second side immersible into said liquid as a liquid/wedge interface whereby a first ultrasonic signal emanating from said first ultrasonic transducer strikes said second side and reflects to a third non-parallel side as a first angle to a second ultrasonic transducer, wherein the improvement comprises:

said wedge material further having a second section with a fourth non-parallel side and a third ultrasonic transducer mounted thereon and a fifth non-parallel side substantially parallel to the first side, said fifth side in contact with a gas forming a gas/wedge interface whereby a second ultrasonic signal strikes said fifth parallel side; and said second section is substantially ultrasonically similar to said first section.

7. The ultrasonic densitometer as recited in claim 6, wherein said gas/wedge interface is a gas pocket in said wedge material covered by a plate.

8. The ultrasonic densitometer as recited in claim 6, further comprising a second pair of non-parallel sides with transducers thereon thereby forming a second angle for obtaining ultrasonic reflection from the liquid/wedge interface.

9. A method of measuring density of a liquid comprising the steps of:

placing a wedge material in contact with said liquid, said wedge material having a first section with a liquid/wedge interface, a first and second transducer as a first pair of transducers mounted on a first pair of opposing surfaces that are non-parallel to said liquid/wedge interface as a first angle, wherein the improvement comprises:

(a) providing a second section with a gas/wedge interface and substantially ultrasonically similar to said first section and having a second pair of transducers mounted on a pair of opposing surfaces that are non-parallel to said gas/wedge interface as a second angle corresponding to the first angle of the first section;

(b) emitting ultrasonic signals from transmitting transducers to said liquid/wedge interface and to said gas/wedge interface; receiving reflected ultrasonic signals reflected from said interfaces;

(c) obtaining a set of parameters from said received reflected ultrasonic signals within said first section and from said received reflected ultrasonic signals within said second section; and (d) computing density from said sets of parameters.

10. The method as recited in claim 9, wherein said set of parameters is speed of sound and acoustic impedance obtained from said first section and a sign of a reflection coefficient obtained from said second section.

11. The method as recited in claim 9, wherein the set of parameters is a phase between reflections obtained from the first and second sections.

12. The method as recited in claim 9, wherein a second pair of non-parallel sides and transducers thereon provide a third angle of ultrasonic signals on the first section wherein the ultrasonic signals from the first, second and third angles are expanded into a matrix of acoustic impedance and speed of sound that are subjected to a $\chi^2$ analysis.

* * * * *